(12) United States Patent
Matsui

(10) Patent No.: US 6,410,525 B1
(45) Date of Patent: Jun. 25, 2002

(54) CARBAPENEM DERIVATIVES, UTILIZATION THEREOF AND INTERMEDIATE COMPOUNDS OF THE SAME

(75) Inventor: Hiroshi Matsui, Nara (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 09/674,363

(22) PCT Filed: Apr. 28, 1999

(86) PCT No.: PCT/JP99/02301

§ 371 (c)(1),
(2), (4) Date: Oct. 31, 2000

(87) PCT Pub. No.: WO99/57121

PCT Pub. Date: Nov. 11, 1999

(30) Foreign Application Priority Data

May 1, 1998 (JP) .......................................... 10-122499
Jul. 17, 1998 (JP) .......................................... 10-203730

(51) Int. Cl.$^7$ .................... C07D 477/20; A61K 31/407; A61P 31/04
(52) U.S. Cl. .................... 514/210.13; 540/350
(58) Field of Search ...................... 540/350; 514/210.13

(56) References Cited

U.S. PATENT DOCUMENTS

| | | | |
|---|---|---|---|
| 4,740,507 A | 4/1988 | Sugimura et al. | |
| 4,888,344 A | 12/1989 | Sunagawa et al. | |
| 4,933,333 A | 6/1990 | Sunagawa et al. | |
| 5,104,867 A | 4/1992 | Kawamoto | 514/210 |
| 5,242,914 A | 9/1993 | Kawamoto | 514/210 |
| 5,523,415 A | 6/1996 | Sendo et al. | |
| 5,866,564 A | 2/1999 | Kawamoto et al. | |
| 6,090,802 A | 7/2000 | Kawamoto et al. | |

FOREIGN PATENT DOCUMENTS

| | | |
|---|---|---|
| EP | 0472062 | 2/1992 |
| JP | 60-233076 | 11/1985 |

OTHER PUBLICATIONS

Sunagawa, et al., "Synthesis and Biological Properties of 1β–Methyl–Carbapenems with N–Methylpyrrolidinylthio Group At C–2 Position", The Journal of Antibiotics, 1992, vol. 45, No. 6, pp. 971–976.

Sunagawa, et al., "Synthesis and Antibacterial Activity of Novel Carbapenems with a Catechol or Hydroxypyridone Moiety", The Journal of Antibiotics, 1994, vol. 47, No. 11, pp. 1354–1358.

Sunagawa, et al., "A Novel Carbapenem Antibiotic, SM–7338 Structure–Activity Relationships", The Journal of Antibiotics, 1990, vol. 43, No. 5, pp. 519–532.

Abstracts of the 36$^{th}$ Interscience Conference on Antimicrobial Agents and Chemotherapy, vol. 36, No. 0, 1996, p. 118, poster F107.

Abstracts of the 35$^{th}$ Interscience Conference on Antimicrobial Agents and Chemotherapy, vol. 35, No. 0, 1995, p. 136, poster F133.

Sunagawa, et al., "Structure–activity Relationship of 1β–Methyl–Carbapenem to Its Antibacterial Activity: Effect of the C–2 Side Chain and the 1β–Methyl Group", The Journal of Antibiotics, 1996, vol. 49, No. 11, pp. 1175–1178.

Abstract and claims of HU 204275B (Dec. 1991).
Claims of HU 211836A9.

*Primary Examiner*—Mark L. Berch
(74) *Attorney, Agent, or Firm*—Wenderoth, Lind & Ponack, L.L.P.

(57) ABSTRACT

A carbapenem compound of the formula (I)

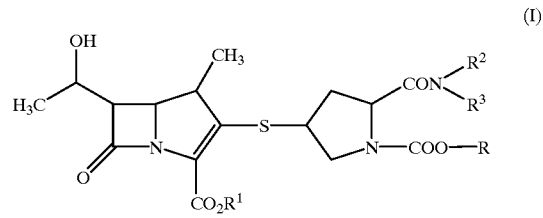

(I)

wherein $R^1$ is a group hydrolyzable in the living body, $R^2$ and $R^3$ are the same or different and each is a lower alkyl, R is a group of the formula (B) or (C)

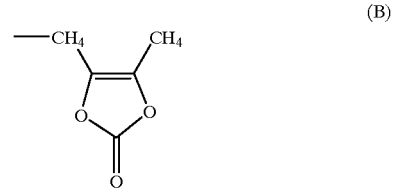

(B)

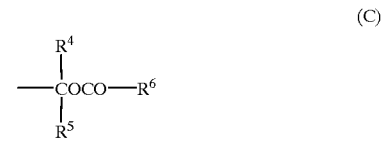

(C)

wherein $R^4$ and $R^5$ are the same or different and each is a hydrogen atom or a lower alkyl and $R^6$ is an alkyl having 1 to 10 carbon atoms. The carbapenem compound (I) of the present invention is superior in absorption from the digestive tract upon oral administration and shows sufficient antibacterial property against a broad range of bacteria species. Therefore, the compound is extremely useful for the prophylaxis and treatment of infectious diseases (particularly bacterial infection).

11 Claims, No Drawings

CARBAPENEM DERIVATIVES, UTILIZATION THEREOF AND INTERMEDIATE COMPOUNDS OF THE SAME

TECHNICAL FIELD

The present invention relates to a novel carbapenem compound useful as an agent for the prophylaxis and treatment of bacterial infectious diseases. More particularly, the present invention relates to a novel carbapenem compound having sufficient antibacterial property and permitting oral absorption, an oral antibacterial agent containing this compound as an active ingredient and an intermediate compound for the production of the carbapenem compound.

BACKGROUND ART

A number of compounds having a carbapenem skeleton have been heretofore found to be a therapeutic agent for infectious diseases, and some of which have been put to practical use for the superior antibacterial activity they possess or have been developed for practical application. For example, a carbapenem compound of the formula (A)

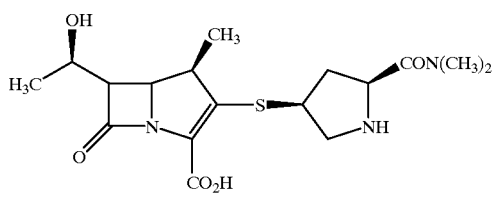

(A)

has already been put to practical use in clinical situations. This carbapenem compound has a broad antibacterial spectrum and a strong antibacterial activity, and has overcome instability of the conventional carbapenem compound to renal dehydropeptidase, which was considered a defect of this compound. It has superior characteristic feature in that it can be administered alone without using a stabilizer.

On the other hand, this carbapenem compound shows poor absorption from the digestive tract and is now administered as an injection in clinical use. An oral agent is easily and conveniently administered and is clinically extremely useful as compared to injections. Therefore, there is a strong demand for the development of carbapenem compound for oral administration, that has a strong antibacterial activity and a broad antibacterial spectrum, and that shows superior absorption from the digestive tract.

DISCLOSURE OF THE INVENTION

It is therefore an object of the present invention to provide a carbapenem compound having a superior antibacterial property and showing superior absorption from the digestive tract. Another object of the present invention is to provide use of the carbapenem compound. A yet another object of the present invention is to provide an intermediate suitable for the production of the carbapenem compound.

The present inventor has conducted intensive studies in an attempt to achieve the above-mentioned objects and found that a novel carbapenem compound of the following formula (I) shows superior absorption from the digestive tract, that the compound has sufficiently strong antibacterial property and is extremely useful as an oral antibacterial agent. He has also found a novel intermediate compound usable for the production of this compound, which resulted in the completion of the present invention.

Accordingly, the present invention provides the following (1) to (10).

(1) A carbapenem compound of the formula (I)

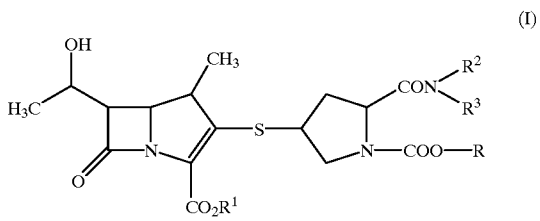

(I)

wherein $R^1$ is a modifier hydrolyzable in the living body, $R^2$ and $R^3$ are the same or different and each is a lower alkyl and R is a group of the formula (B)

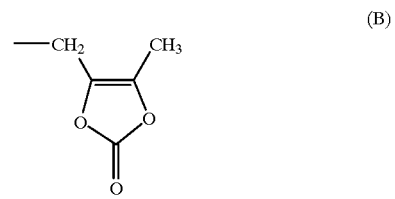

(B)

or formula (C)

(C)

wherein $R^4$ and $R^5$ are the same or different and each is a hydrogen atom or a lower alkyl and $R^6$ is an alkyl having 1 to 10 carbon atoms.

(2) The carbapenem compound of (1) above, wherein $R^2$ and R3 are the same or different and each is a lower ally.

(3) The carbapenem compound of (1) above, wherein $R^1$ is pivaloyloxymethyl.

(4) The carbapenem compound of (1) above, wherein $R^1$ is 1-cyclohexyloxycarbonyloxyethyl.

(5) The carbapenem compound of (1) above, wherein $R^1$ is 1-ethoxycarbonyloxyethyl.

(6) The carbapenem compound of (1) above, which is a member selected from the group consisting of:

pivaloyloxymethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate, 1-cyclohexyloxycarbonyloxyethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2em-3carboxylate, 1-ethoxycarbonyloxyethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate, pivaloyloxymethyl (1R,5S,6S)-2-[(3S,5S)-(5-N,N-dimethylaminocarbonyl-1-acetyloxymethyloxycarbonyl)pyrrolidin-3-ylthio[-6-(1R)-1-hydroxyethyl]-1-methylcarbapen-2-em-3-carboxylate, pivaloyloxymethyl (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2em-3carboxylate, pivaloyloxymethyl (1R,5S,6S)-2-[(3S,5S)-(5-N,N-dimethylaminocarbonyl-1-isobutyryloxymethyloxycarbonyl)pyrrolidin-3-ylthio]-6-(1R)-1-hydroxyethyl]-1-methylcarbapen-2-em-3carboxylate, pivaloyloxymethyl (1R,5S,6S)-2-[(3S,5S)-(5-N,N-dimethylaminocarbonyl-1-pivaloyloxymethyloxycarbonyl)pyrrolidin-3-ylthio]-6-[(1R)-1-[hydroxyethyl]-1-methylcarbapen-2-em-3carboxylate, pivaloyloxymethyl (1R,5S,6S)-2-[(3S,5S)-(5-N,N-dimethylaminocarbonyl-1-isovaleryloxymethyloxycarbonyl)pyrrolidin-3-ylthio]-6-(1R)-1-hydroxyethyl]-1-methylcarbapen-2em-3 carboxylate, pivaloyloxymethyl (1R,5S,6S)-2-[(3S,5S)-(5-N,N-dimethylaminocarbonyl-1-tert-butylacetyloxymethyloxycarbonyl)pyrrolidin-3-ylthio]-6-[(1R)-1-hydroxyethyl]-1-methylcarbapen-2-em-3-carboxylate, 1-cyclohexyloxycarbonyloxyethyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2em-3-carboxylate, and 1-ethoxycarbonyloxyethyl (1R,5S,6S)-2-[(3S,5S)-(5-N,N-dimethylaminocarbonyl-1-pivaloyloxymethyloxycarbonyl)pyrrolidin-3-ylthio]-6-[(1R)-1-hydroxyethyl]-1-methylcarbapen-2em-3-carboxylate.

(7) An antibacterial agent comprising the carbapenem compound of (1) above of the formula (I) as an active ingredient.

(8) The antibacterial agent of (7), which is for oral administration.

(9) A carbapenem compound of the formula (II)

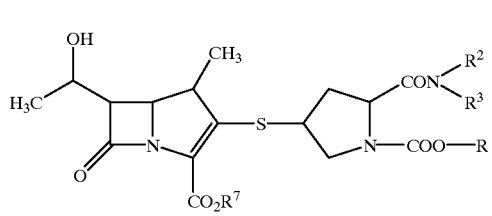

(II)

wherein $R^2$ and $R^3$ are the same or different and each is a lower alkyl, $R^7$ is a hydrogen atom or a protecting group of carboxyl group and R is a group of the formula (B)

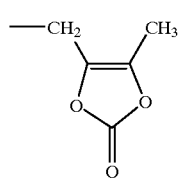

(B)

or formula (C)

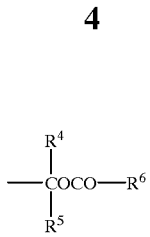

(C)

wherein $R^4$ and $R^5$ are the same or different and each is a hydrogen atom or a lower alkyl and $R^6$ is an alkyl having 1 to 10 carbon atoms, or a salt thereof.

(10) The carbapenem compound of (9) above, which is a member selected from the group consisting of:

p-nitrobenzyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R-1-hydroxyethyl]-1-methylcarbapen-2-em-3-carboxylate, (1R,5S,6S)-2{-(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylic acid, p-nitrobenzyl (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate, p-nitrobenzyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2-em-3-carboxylate, (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylic acid, and (1R,5S,6S)-2-[(3S,5S)-(5-N,N-dimethylaminocarbonyl-1-isobutyryloxymethyloxycarbonyl)pyrrolidin-3-ylthio]-6-[(1R)-1-1-hydroxyethyl]-1-methylcarbapen-2-em-3-carboxylic acid, or a salt thereof, particularly a sodium salt thereof.

DETAILED DESCRIPTION OF THE INVENTION

The definitions used in the present specification are explained in the following.

The "modifier hydrolyzable in the living body" at $R^1$ is preferably hydrolyzable in intestine or blood. Examples thereof include optionally substituted aryl (e.g., phenyl, tolyl, xylyl, indanyl and the like), 1-alkanoyloxyalkyl, 1-alkoxycarbonyloxyal, phthalidyl, 5-methyl-2-oxo-1, 3dioxolen-4-ylmethyl and the like, with preference given to 1-alkanoyloxyallyl, 1-alkoxycarbonyloxyalkyl and 5-methyl-2-oxo-1,3-dioxolen-4-ylmethyl.

The "optionally substituted aryl" is preferably an unsubstituted aryl or aryl optionally substituted by 1 to 3 substituent(s), wherein the substituents may be the same or different. Examples of the substituent include allyl having 1 to 4 carbon atoms such as methyl, ethyl and the like.

The number of carbon atoms of the alkanoyl moiety of "1-alkanoyloxyalkyl" is preferably 2 to 10, more preferably 2 to 7, which may be linear, branched or cyclic. The number of carbon atom(s) of the alkyl moiety is preferably 1 to 3, more preferably 1 or 2.

Examples of 1-alkanoyloxyalkyl include acetoxymethyl, propionyloxymethyl, n-butyryloxymethyl, isobutyryloxymethyl, pivaloyloxymethyl, n-valeryloxymethyl, 2-methylbutyryloxymethyl, isovaleryloxymethyl, n-hexanoyloxymethyl, 3-methylvaleryloxymethyl, neohexanoyloxymethyl, 2-methylhexanoyloxymethyl, 2,2-dimethylvaleryloxymethyl, neoheptanoyloxymethyl, cyclohexanecarbonyloxymethyl, cyclohexylacetoxymethyl, 1-acetoxyethyl, 1-propionyloxyethyl, 1-n-butyryloxyethyl, 1-isobutyryloxyethyl, 1-n-valeryloxyethyl, 1-pivaloyloxyethyl, 1-isovaleryloxyethyl, 1-n-hexanoyloxyethyl, 1-cyclohexanecarbonyloxyethyl and the like.

The number of carbon atom(s) of the alkoxy moiety of "1-alkoxycarbonyloxyalkyl" is preferably 1 to 10, more preferably 1 to 7, which may be linear, branched or cyclic. The number of carbon atom(s) of the alkyl moiety is preferably 1 to 3, more preferably 1 or 2.

Examples of "1-alkoxycarbonyloxyalkyl" include 1-methoxycarbonyloxyethyl, 1ethoxycarbonyloxyethyl, 1-n-propoxycarbonyloxyethyl, 1-isopropoxycarbonyloxyethyl, 1-n-butoxycarbonyloxyethyl, 1-secbutoxycarbonyloxyethyl, 1-t-butoxycarbonyloxyethyl, 1-pentyloxycarbonyloxyethyl, 1cyclohexyloxycarbonyloxyethyl and the like.

The "lower alkyl" at $R^2$, $R^3$, $R^4$ and $R^5$ is a linear or branched alkyl having 1 to 6 carbon atoms, which is exemplified by methyl, ethyl, propyl, isopropyl, butyl, isobutyl, sec-butyl, t-butyl, pentyl, isopentyl, neopentyl, t-pentyl, hexyl, isohexyl, neohexyl and the like. Of these, methyl, ethyl, propyl and butyl are preferable.

The "alkyl" at $R^6$ is a linear, branched or cyclic alkyl having 1 to 10 carbon atoms, which is exemplified by methyl, ethyl, propyl, isopropyl, butyl, isobutyl, sec-butyl, t-butyl, pentyl, isopentyl, neopentyl, t-pentyl, cyclopentyl, hexyl, isohexyl, neohexyl, sec-hexyl, t-hexyl, cyclohexyl, heptyl, isoheptyl, neoheptyl, sec-heptyl, t-heptyl, octyl, isooctyl, neooctyl, sec-octyl, t-octyl and the like.

The "protecting group of carboxyl group" at $R^7$ is exemplified by t-butyl, neopentyl, benzyl, p-nitrobenzyl, p-methoxybenzyl, diphenylmethyl, p-nitrophenyl, methoxymethyl, ethoxymethyl, benzyloxymethyl, methylthiomethyl, trityl, 2,2,2-trichloroethyl, trimethylsilyl, diphenylmethoxybenzenesulfonylmethyl, dimethylaminoethyl and the like. Of these, p-nitrobenzyl, p-methoxybenzyl and diphenylmethyl are preferable.

When the carbapenem compound (II) has a carboxyl group (when $R^7$ is a hydrogen atom), a salt can be formed at the carboxyl group. The salt at the carboxyl group is, for example, alkali metal salt (e.g., sodium salt, potassium salt and the like), alkaline earth metal salt (e.g., calcium salt, magnesium salt and the like), salt of organic base (e.g., triethylamine salt, dicyclohexylamine salt, pyridine salt and the like), and the like.

Examples of preferable carbapenem compound (I) of the present invention include the following.
Pivaloyloxymethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
1-cyclohexyloxycarbonyloxyethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
1-ethoxycarbonyloxyethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
pivaloyloxymethyl (1R,5S,6S)-2-{(3S,5S)-[5-N,N-diethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
pivaloyloxymethyl (1R,5S,6S)-2-[(3S,5S)-(5-N-ethyl-N-methylaminocarbonyl-1-(5-methyl-2-oxo-1,3-dioxolen-4-yl)methyloxycarbonyl)pyrrolidin-3-ylthio]-6-[(1R)-1-hydroxyethyl]-l-methylcarbapen-2-em-3-carboxylate,
pivaloyloxymethyl (1R,5S,6S)-2-[(3S,5S)-(5-N,N-dimethylaminocarbonyl-1-acetyloxymethyloxycarbonyl)pyrrolidin-3-ylthio]-6-[(1R)1 -hydroxyethyl]-1-methylcarbapen-2-em-3-carboxylate,
pivaloyloxymethyl (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2em-3-carboxylate,
pivaloyloxymethyl (1R,5S,6S)-2-[(3S,5S)-(5-N,N-dimethylaminocarbonyl-1-pivaloyloxymethyloxycarbonyl)pyrrolidin-3-ylthio]-6-[(1R)-1-hydroxyethyl]-1-methylcarbapen-2em-3-carboxylate,
pivaloyloxymethyl (1R,5S,6S)-2-[(3S,5S)-(5-N,N-dimethylaminocarbonyl-1-isovaleryloxymethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N,N-dinethylaminocarbonyl-1-tert-butylacetyloxymethyloxycarbonyl)pyrrolidin-3-ylthio]-6-[(1R)-1-hydroxyethyl]-1-methylcarbapen-2-em-3-carboxylate,
1-cyclohexyloxycarbonyloxyethyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2em-3-carboxylate,
1-ethoxycarbonyloxyethyl (1R,5S,6S)-2-[(3S,5S)7(5-N,N-dimethylaminocarbonyl-1-pivaloyloxymethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N-ethyl-N-methylaminocarbonyl-1-propionyloxymethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N,N-diethylaminocarbonyl-1-propionyloxymethyloxycarbonyl)pyrrolidin-3-ylthio]-6-[(1R)-1-hydroxyethyl]-1-methylcarbapen-2-em-3-carboxylate, and the like.

Examples of preferable carbapenem compound (II) of the present invention include the following.
p-Nitrobenzyl (1R,5S,6S)-2-{(3S,5S)-[5-N,N-dimethylaminocarbonyl-1-(5 -methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate, sodium (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate, p-nitrobenzyl (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate, p-nitrobenzyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-11-methylcarbapen-2-em-3-carboxylate, sodium (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate, sodium (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2em-3-carboxylate, and the like.

The carbapenem compound (I) and carbapenem compound (II), which is an intermediate compound thereof, can be produced by any of the following methods 1 to 5.

Production Method 1

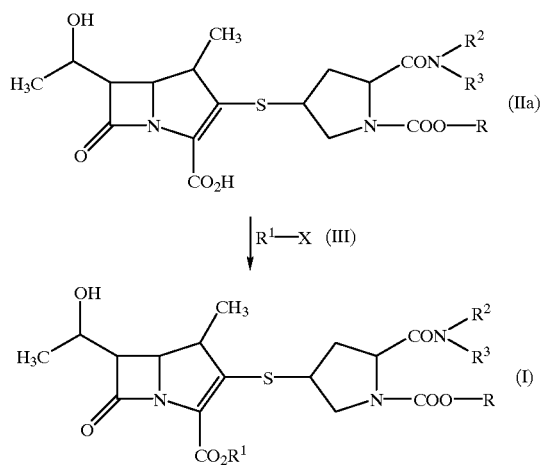

wherein $R^1$, $R^2$, $R^3$ and R are as defined above, and X is a halogen atom such as chlorine, bromine, iodine and the like, a leaving group such as alkanesulfonyloxy (e.g., methanesulfonyloxy, ethanesulfonyloxy, propanesulfonyloxy, butanesulfonyloxy and the like), arylsulfonyloxy (e.g., phenylsulfonyloxy, tolylsulfonyloxy and the like), and the like.

The compound (I) is obtained by dissolving compound (IIa) in a solvent that does not interfere with the reaction (e.g., dioxane, acetonitrile, tetrahydrofuran, chloroform, methylene chloride, ethylene chloride, benzene, ethyl acetate, N,N-dimethylformamide, N,N-dimethylacetamide, dimethyl sulfide, and a mixture thereon) and reaction with compound (III) in an equimolar to 5-fold molar amount, preferably about equimolar to bimolar amount, in the presence of a base.

The base to be used is free of particular limitation and is exemplified by inorganic base (e.g., sodium hydrogencarbonate, potassium carbonate and the like), organic base (e.g., triethylamine, diisopropylethylamine, pyridine and the like), and the like.

While the reaction temperature is not particularly limited, the reaction proceeds at a comparatively low temperature to suppress side reactions, which is exemplified by −30° C. to 40° C., preferably −10° C. to 10° C. The reaction time varies mainly due to the reaction temperature, kind of the reaction reagent and the like and is generally from 30 minutes to dozen and odd hours.

The compound (IIa) may be converted to a reactive derivative thereof, such as alkali metal salt (e.g., sodium salt, potassium salt and the like), alkaline earth metal salt (e.g., calcium salt and the like), triethylamine salt, dicyclohexylamine salt, pyridine salt and the like, and then reacted with compound (III).

Production Method 2

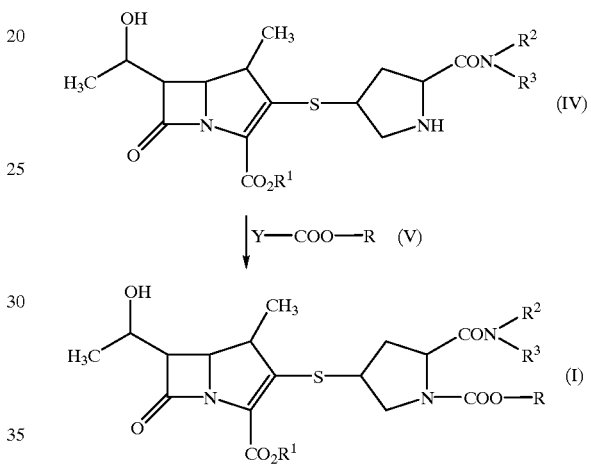

wherein $R^1$, $R^2$, $R^3$ and R are as defined above and Y is a leaving group such as chlorine, imidazol-1-yl, p-nitrophenyloxy, 2-phenylacetonitril-2-yl-iminooxy and the like.

The compound (I) can be obtained by dissolving compound (IV) in a solvent that does not interfere with the reaction (e.g., dioxane, acetonitrile, tetrahydrofuran, chloroform, methylene chloride, ethylene chloride, benzene, ethyl acetate, N,N-dimethylformamide, N,N-dimethylacetamide, dimethyl sulfoxide, and a mixture thereof) and reaction with compound (V) in an equimolar to 5-fold molar amount, preferably about equimolar to bimolar amount The compound (IV) can be obtained in the same manner as in Production Method 1 by reacting compound (III) with the carboxylic acid disclosed in JP-A-60-233076 and the like.

The reaction can be also carried out in the presence of a base. The base to be used is free of particular limitation and is preferably exemplified by inorganic base (e.g., sodium hydrogencarbonate, potassium carbonate and the like), organic base (e.g., triethylamine, diisopropylethylamine, pyridine and the like), and the like.

While the reaction temperature is not particularly limited, the reaction proceeds at a comparatively low temperature to suppress side reactions, which is exemplified by −30° C. to 40° C., preferably −10° C. to 10° C. The reaction time varies manly due to the reaction temperature, kind of the reaction reagent and the like and is generally from 30 minutes to dozen and odd hours.

Production Method 3

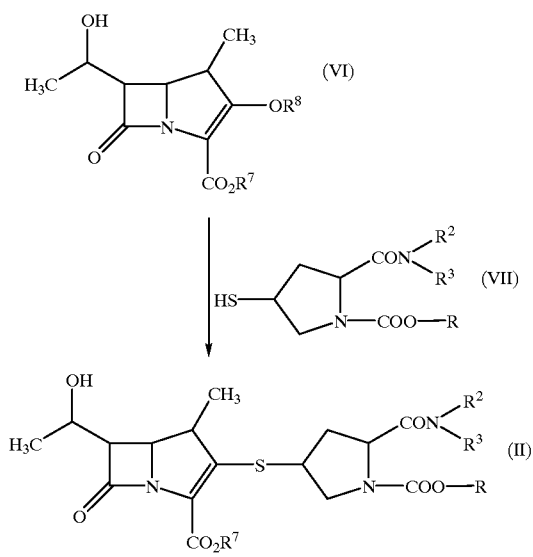

wherein $R^2$, $R^3$, $R^7$ and R are as defined above, and $R^8$ is alkanesulfonyl (e.g., methanesulfonyl, ethanesulfonyl, propanesulfonyl, butanesulfonyl and the like), arylsulfonyl (e.g., phenylsulfonyl, tolylsulfonyl and the like), dialkylphosphorl (e.g., dimethylphosphoryl, diethylphosphoryl, diisopropylphosphoryl, dibutylphosphoryl and the like), diarylphosphoryl (e.g., diphenylphosphoryl, ditolylphosphoryl and the like).

The compound (II) can be obtained by dissolving compound (VI) disclosed in Japanese Patent Unexamined Publication No. 8-12676 and the like in a solvent that does not interfere with the reaction (e.g., dioxane, acetonitrile, tetrahydrofuran, chloroform, methylene chloride, ethylene chloride, benzene, ethyl acetate, N,N-dimethylformamide, N,N-dimethylacetamide, dimethyl sulfoxide, and a mixture thereof) and reaction with mercapto compound (VII) in an equimolar to 5-fold molar amount, preferably about equimolar to 3-fold molar amount in the presence of a base.

The base to be used is free of particular limitation and is exemplified by inorganic base (e.g., sodium hydrogencarbonate, potassium carbonate and the like), organic base (e.g., triethylamine, diisopropylethylamine, pyridine and the like), and the like.

While the reaction temperature is not particularly limited, the reaction proceeds at a comparatively low temperature to suppress side reactions, which is exemplified by −30° C. to 40° C., preferably −10° C. to 10° C. The reaction time varies mainly due to the reaction temperature, kind of the reaction reagent and the like and is generally from 30 minutes to dozen and odd hours.

The compound (VII), which is a staring material for the synthesis for compound (II), is prepared in the following manner.

Production Method of Compound (VII)

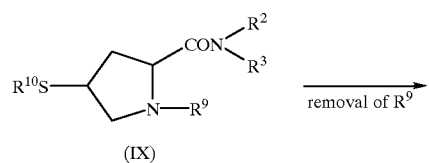

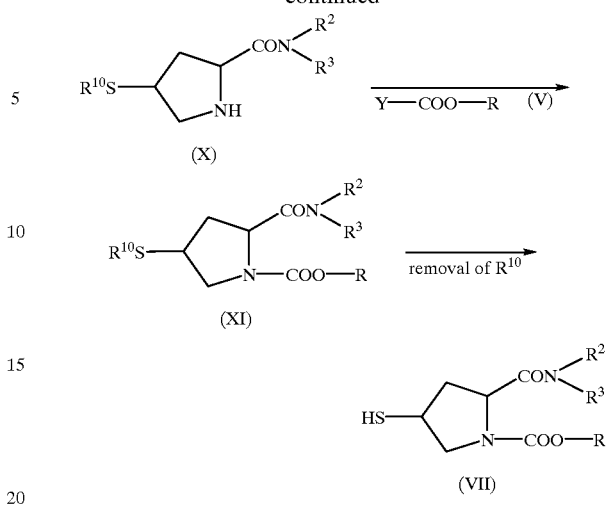

wherein $R^2$, $R^3$, R and Y are as defined above, $R^9$ is an amino-protecting group and $R^{10}$ is a thiol-protecting group.

The compound (VII) can be synthesized by removing $R^9$, which is an amino-protecting group of compound (IX) disclosed in JP-A-60-233076 and the like, by a method known in the filed to give compound (X), the reacting compound (X) and compound (V) in the same manner as in Production Method 2 to give compound (XI), and removing $R^{10}$ which is a thiol-protecting group by a method known in the field. As the protecting group of thiol and amino, those generally used in the technique in this field can be used.

Production Method 4

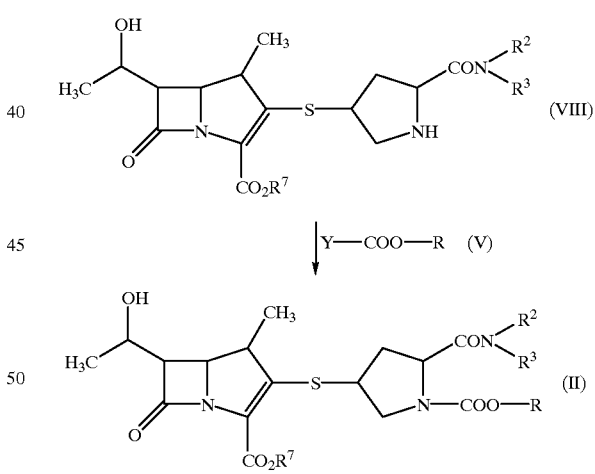

wherein $R^2$, $R^3$, $R^7$, R and Y are each as defined above.

The compound (II) can be obtained by reacting compound (VIII) disclosed in JP-A-60-233076 and the like and compound (V) in the same manner as in Production Method 2.

The carbapenem compound (II) thus obtained can be converted to a carboxylic acid derivative wherein $R^7$ is hydrogen atom, by removing the carboxyl-protecting group as necessary by a conventional method. While the method for removing a protecting group varies depending on the kind thereof, a method generally used in the technique in this field can be used.

Production Method 5

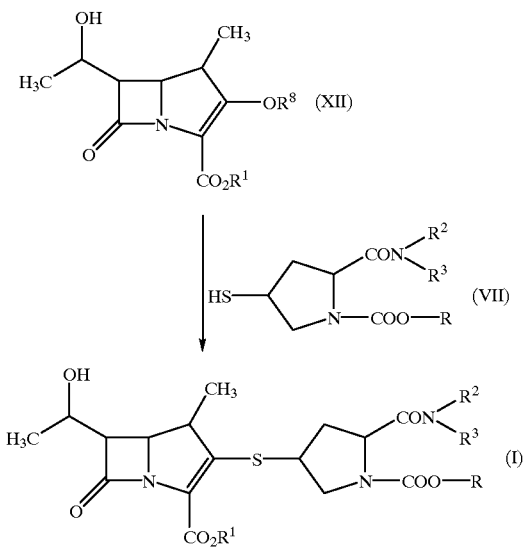

wherein $R^1$, $R^2$, $R^3$, $R^8$ and R are as defined above.

The compound (I) can be obtained by dissolving compound (XII) in a solvent that does not interfere with the reaction (e.g., dioxane, acetonitrile, tetrahydrofuran, chloroform, methylene chloride, ethylene chloride, benzene, ethyl acetate, N,N-dimethylformamide, N,N-dimethylacetamide, dimethyl sulfoxide, and a mixture thereof and reaction with mercapto compound (VII) in an equimolar to 5-fold molar amount, preferably about equimolar to 3-fold molar amount, in the presence of a base.

The base to be used is free of particular limitation and is exemplified by inorganic base (e.g., sodium hydrogencarbonate, potassium carbonate and the like), organic base (e.g., triethylamine, diisopropylethylamine, pyridine and the like), and the like.

While the reaction temperature is not particularly limited, the reaction proceeds at a comparatively low temperature to suppress side reactions, which is exemplified by −30° C. to 40° C., preferably −10° C. to 10° C. The reaction time varies mainly due to the reaction temperature, kind of the reaction reagent and the like and is generally from 30 minutes to dozen and odd hours.

The carbapenem compound (I) and carbapenem compound (II) can be purified as necessary according to a conventional method, such as recrystallization, preparative thin-layer chromatography, column chromatography and the like. Where necessary, it can be purified as a salt thereof.

The preferable configuration of the compound (I) and compound (II) which are the objects of the present invention are the following compound (Ia) and compound (IIb).

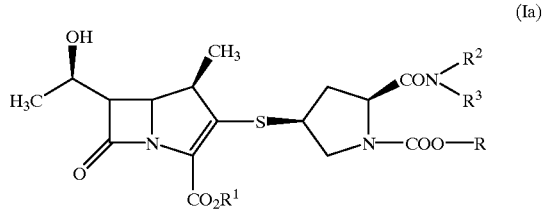

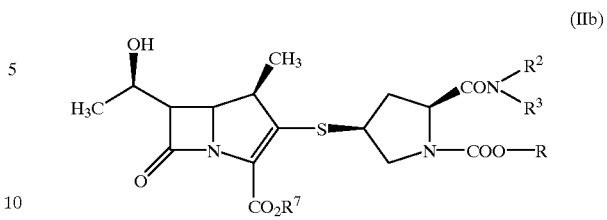

wherein $R^2$, $R^3$, $R^7$ and R are as defined above.

The carbapenem compound (I) after oral administration can be rapidly absorbed into blood and converts to a metabolite, i.e., carbapenem compound wherein, in the formula (IV), $R^1$ is hydrogen atom, that shows high concentration in blood.

Hence, an agent for the prophylaxis and treatment of infectious diseases, which comprises carbapenem compound (I) shows superior action mentioned above by oral administration and is generally administered as an oral agent.

The agent for the prophylaxis and treatment of infectious diseases can be produced by dilution with a pharmaceutical excipient according to a method known in the field. Examples of the excipient include starch, lactose, sugar, calcium carbonate, calcium phosphate and the like.

The agent for the prophylaxis and treatment of infectious diseases can contain other preferable additives where desired, such as a binder (e.g., starch, gum arabic, carboxymethylcellulose, hydroxypropylcellulose, crystalline cellulose and the like), a lubricant (e.g., magnesium stearate, talc and the like), a disintegrator (e.g., calcium carboxymethylcellulose, talc and the like), and the like. After admixing each ingredient, the mixture is formulated into a suitable dosage form suitable for oral administration, such as capsule, tablet, fine particle, granule, dry syrup and the like by a method known in the field, whereby an agent for oral administration for the prophylaxis and treatment of infectious diseases can be produced.

The daily dose of carbapenem compound (I), which is subject to change according to the administration target, symptom and the like, is about 1–40 mg/kg body weight/dose for oral administration to an adult patient with a purulent disease, wherein the administration frequency is 1 to 4 times a day.

The carbapenem compound (I) can be used in conjunction with other substance having an antibacterial activity, such as an antibacterial agent (penicillins, aminoglycosides, cephalosporins and the like) or a therapeutic agent for systemic symptom caused by bacterial infection (e.g., antipyretic, analgesic, antiphlogistic and the like).

EXAMPLES

The present invention is explained with respect to the physical property and production method in the following by way of Examples which do not limit the present invention in any way.

Example 1 p-nitrobenzyl (1R,5S,6S)-2-{(3S,5S)-[5-N,N-dimethylaminocarbonyl-1-(5-methyl-2oxo-1,3-dioxolen-4-yl)methyloxycarbonyl]pyrrolidin-3-ylthio}-6-[(1R)-1-hydroxyethyl]-1-methylcarbapen-2-em-3-carboxylate (2S,4S)-2-N,N-Dimethylaminocarbonyl-4-mercapto-1-(5-methyl-2-oxo-1,3-dioxolen-4-yl)

methyloxycarbonylpyrrolidine(179 mg) was dissolved in acetonitrile (11 ml) and p-nitrobenzyl (1R,5S,6S)-2-diphenylphosphoryl-6-[(1R)-1-hydroxyethyl]-1-methylcarbapen-2-em-3-carboxylate (1.15 g) and diisopropylethylamine (0.38 ml) were added at 0° C. under a nitrogen atmosphere. After mixing for one hour at the same temperature, ethyl acetate (200 ml) was added. The mixture was washed with saturated brine (100 ml) and dried over anhydrous sodium sulfate. Ethyl acetate was evaporated under reduced pressure and the residue was purified by silica gel column chromatography to give the title compound (911 mg).

$^1$H-NMR(CDCl$_3$, δ ppm): 1.27(3H,d), 1.33(3H,d), 1.7–2.1, 2.5–2.9(2H,m), 2.17(3H,s), 2.8–4.4(13H,m), 4.6–5.6(5H,m), 7.64, 8.20(4H,A$_2$'B$_2$').

Example 2

Sodium (1R,5S,6S)-2-{(3S,5S)-[5-N,N-dimethylaminocarbonyl-1-(5-methyl-2-oxo-1,3-dioxolen-4-yl)methyloxycarbonyl]pyrimidin-3-ylthio}-6-[(1R)-1-hydroxyethyl]-1-methylcarbapen-2em-3-carboxylate p-Nitrobenzyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate (330 mg) was dissolved in a mixture of tetrahydrofuran (17 ml) and 0.1 M MOPS buffer (pH 7.0, 17 ml). 10% Palladium carbon (330 mg) was added and the mixture was hydrogenated at room temperature for 16 hr. The reaction mixture was passed through celite, and the filtrate was washed with diethyl ether and concentrated under reduced pressure to about 5 ml. The resultant solution was subjected to chromatography using DIAION HP-21 (manufactured by Mitsubishi Chemical), concentrated under reduced pressure and lyophilized to give the title compound (130 mg). IR(Nujol, cm$^{-1}$): 3393,1819,1767,1707,1643

$^1$H-NMR(DMSO-d$_6$, δ ppm): 1.16(3H,d), 1.4–1.9(1H,m), 2.13(3H,s), 2.82(3H,s), 3.01(3H,brs), 4.5–5.0(3H,m).

Example 3 pivaloyloxymethyl (1R,5S,6S)-2-{(3S,5S)-[5-N,N-dimethylaminocarbonyl-1-(5 -methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate Sodium (1R,5S,6S)-2-{(3S,5S)-[5-N,N-dimethylaminocarbonyl-1-(5-methyl-2-1,3-dioxolen-4yl)metyloxycarbonyl]pyrrolidin-3-ylthio}-6-[(1R)-1-hydroxyethyl]-1-methylcarbapen-2em-3-carboxylate (960 mg) was dissolved in N,N-dimethylformamide (6 ml) and the mixture was cooled to 5° C. Pivaloyloxymethyl iodide (700 mg) was added and the mixture was stilled at the same temperature for 1 hr and at 35° C. for 12 hr. Ethyl acetate (150 ml) was added, and the mixture was washed with 5% brine (100 ml) and dried over anhydrous sodium sulfate. Ethyl acetate was evaporated under reduced pressure and the residue was purified by silica gel column chromatography to give the title compound (350 mg).

IR(Nujol, cm$^{-1}$): 3404,1821,1780,1715,1651.

$^1$H-NMR(CDCl$_3$, δ ppm): 1.22(9H,s), 1.26(3H,d), 1.31 (3H,d), 1.6–2.1, 2.5–2.9(2H,m), 2.17(3H,s), 2.8–4.4(13H, m), 4.80(1H,m), 4.72, 4.99(2H,ABq,J=13.2 Hz), 5.87, 5.92 (2H,ABq,J=5.5 Hz).

Example 4 pivaloyloxymethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl-1-methylcarbapen-2-em-3-carboxylate (1) Sodium (1R,5S,6S)-2-[(3S,5S)-5-N,N-dimethylaminocarbonylpyrrolidin-4-ylthio]-6-[(1R-1-hydroxyethyl-]-1-methylcarbapen-2-em-3-carboxylate (530 mg) was suspended in N,N-dimethylformamide (2.3 ml) and the suspension was cooled to 5° C. Pivaloyloxymethyl iodide (819 mg) was added and the mixture was stirred at the same temperature for 1 hr. Ethyl acetate (150 ml) was added, and the mixture was washed with 5% brine (100 ml) and dried over anhydrous sodium sulfate. Ethyl acetate was evaporated under reduced pressure and the residue was purified by silica gel column chromatography to give pivaloyloxymethyl (1R,5S,6S)-2-[(3S,5S)-5-N,N-dimethylaminocarbonylpyrrolidin-4-ylthio]-6-[(1R)-1-hydroxyethyl]-1-methylcarbapen-2-em-3-carboxylate (470 mg).

$^1$H-NMR(CDCl$_3$, δ ppm): 1.22(9H,s), 1.2–1.4(6H,m), 1.5–1.8, 2.4–2.8(2H,m), 2.98(3H,s), 3.02(3H,s), 3.04.4(8H, m), 5.81, 5.95(2H,ABq,J=5.5 Hz).

(2) The compound (497 mg) obtained in (1) was dissolved in methylene chloride (5 ml) and cooled to 5° C. (5-Methyl-2-oxo-1,3-dioxolen-4-yl)methyloxycarbonyl chloride (231 mg) and triethylamine (0.14 ml) were added and the mixture was stirred at the same temperature for 30 min. Ethyl acetate (150 ml) was added and the mixture was washed with 5% brine (100 ml) and dried over anhydrous sodium sulfate. Ethyl acetate was evaporated under reduced pressure and the residue was purified by silica gel column chromatography to give the title compound (140 mg).

Example 5 pivaloyloxymethyl (1R,5S,6S)-2-{(3S,5S)-[5-N,N-dimethylaminocarbonyl-1-(5-methyl-2-oxo-1, 3dioxolen-4-yl)methyloxycarbonyl]pyrrolidin-3-ylthio}-6-[(1R)-1-hydroxyethyl]-1-methylcarbapen-2-em-3-carboxylate The compound (500 mg) obtained in Example 4 (1) was dissolved in N,N-dimethylformamide (2.5 ml). (5-Methyl-2-oxo-1,3-dioxolen-4yl)methyl p-nitrophenyl carbonate (297 mg) and triethylamine (0.14 ml) were added and the mixture was stirred at room temperature for 2 hours. To the reaction mixture was added ethyl acetate (150 ml), and the mixture was washed with 10% citric acid (100 ml), 5% aqueous sodium hydrogencarbonate solution (100 ml) and saturated brine (100 ml), and dried over anhydrous sodium sulfate. Ethyl acetate was evaporated under reduced pressure and the residue was purified by silica gel column chromatography to give the title compound (350 mg).

Example 6

Cyclohexyloxycarbonyloxyethyl (1R,5S,6S)-2-{(3S, 5S)-[5-N,N-dimethylaminocarbonyl-1-(5-methyl-2-oxo-1,3-dioxolen-4-yl)methyloxycarbonyl] pyrrolidin-3-ylthio}-6-[(1R-1-hydroxyethyl]-1-methylcarbapen-2em-3-carboxylate 1-Cyclohexyloxycarbonyloxyethyl (1R,5S,6S)-2-{(3S, 5S)-[5-N,N-dimethylaminocarbonyl]pyrrolidin-3-ylthio}-6-[(1R)-1-hydroxyethyl]-1-methylcarbapen-2-em-3- carboxylate (2.0 g) obtained in the same manner as in Example 4 (1) was dissolved in methylene chloride (20 ml). Thereto were added (5methyl-2-oxo-1,3-dioxolen-4-yl) methyloxycarbonyl chloride (830 mg) and triethylamine (0.50 ml), and the mixture was stirred at room temperature for 2 hr. Thereto was added ethyl acetate (150 ml), and the reaction mixture was washed with 5% brine (100 ml) and dried over anhydrous sodium sulfate. Ethyl acetate was evaporated under reduced pressure and the residue was purified by silica gel column chromatography to give the title compound (680 mg).

IR(Nujol, cm$^{-1}$): 3402,1821,1759,1713, 1647.

$^1$H-NMR(CDCl$_3$, δ ppm): 1.0–2.1(20H,m), 2.16(3H,s), 2.96(3H,s), 3.06, 3.09(3H,s), 3.0–4.4(7H,m), 4.5–5.2(4H, m), 6.7–7.0(1H,q).

Example 7

1-ethoxycarbonyloxyethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-]-ylthio}-6-[(1R)-1-hydroxyethyl]-1-methylcarbapen-2-em-3-carboxylate 1-Ethoxycarbonyloxyethyl (1R,5S,6S)-2-{(3S,5S)-[5-N,N-dimethylaminocarbonyl]pyrrolidin-3-ylthio}-6-[(1R-1-hydroxyethyl]-1-methylcarbapen-2-em-3-carboxylate (1.0 g) obtained in the same manner as in Example 4 (1) was dissolved in N,N-dimethylformamide (5 ml). Thereto were added (5-methyl-2-oxo-1,3-dioxolen-4-yl)methyl p-nitrophenyl carbonate (606 mg) and triethylamine (0.29 ml), and the mixture was stirred at room temperature for 2 hr. Thereto was added ethyl acetate (150 ml), and the reaction m was washed with 5% brine (100 ml) and dried over anhydrous sodium sulfate. Ethyl acetate was evaporated under reduced pressure and the residue was purified by silica gel column chromatography to give the title compound (300 mg).

IR(Nujol, cm$^{-1}$): 3404,1820,1758,1714,1650.

$^1$H-NMR(CDCl$_3$, δ ppm): 1.22(3H,t), 1.27(3H,d), 1.32 (3H,d), 1.51(3H,d), 1.6–2.0, 2.5–2.8(2H,m), 2.16(3H,s), 2.84.4(15H,m), 4.5–5.2(3H,m), 6.7–7.0(1H,q).

Example 8 p-nitrobenzyl (1R,5S,6S)-2-[(3S,5S)-5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate (2S,4S)-2-N,N-Dimethylaminocarbonyl-4-mercapto-1-propionyloxymethyloxycarbonylpyrrolidine (662 mg) was dissolved in acetonitrile (11 ml), and p-nitrobenzyl (1R,5S,6S)-2-diphenylphosphoro-6-[(1R)-1-hydroxyethyl]-1-methylcarbapen-2-em-3-carboxylate (1.15 g) and diisopropylethylamine (0.38 ml) were added at 0° C. under a nitrogen atmosphere. After mixing for one hour at the same temperature, ethyl acetate (200 ml) was added. The mixture was washed with saturated brine (100 ml) and dried over anhydrous sodium sulfate. Ethyl acetate was evaporated under reduced pressure and the residue was purified by silica gel column chromatography to give the title compound (876 mg).

$^1$H-NMR(CDCl$_3$, δ ppm):1.14(3H,t), 1.27(3H,d), 1.33 (3H,d), 1.7–2.1, 2.5–2.40(2H,q), 2.84.4(13H,m), 4.6–5.8 (5H,m), 7.64, 8.20(4H,A$_2$'B$_2$'.

Example 9 sodium (1R,5S,6S)-2-[(3S,5S)-5N,N-dimethylaminocarbonyl-1-propionyloxymethyloxycarbonyl)pyrrolidin-3-ylthio]-6-[(1R)-1-hydroxyethyl]-1-methylcarbapen-2em-3-carboxylate p-Nitrobenzyl (1R,5S,6S)-2-[(3S,5S)-5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate (330 mg) was dissolved in a mixture of tetrahydrofuran (17 ml) and 0.1 M phosphate buffer (pH 7.0, 17 ml). 100% Palladium carbon (330 mg) was added and the mixture was hydrogenated at room temperature for 16 hr. The reaction mixture was passed through celite, and the filtrate was washed with diethyl ether and concentrated under reduced pressure to about 5 ml. The resultant solution was subjected to chromatography using DIAION HP-21 (manufactured by Mitsubishi Chemical), concentrated under reduced pressure and e dried to give the title compound (128 mg).

$^1$H-NMR(DMSO-d$_6$, δ ppm): 1.10(3H,t), 1.17(3H,d), 1.17(3H,d), 1.4–1.9, 2.5–2.7(2H,m), 2.35(2H,q), 2.83(3H, s), 3.02(3H,brs), 4.64.8(1H,t), 5.5–5.7(2H,m).

Example 10 p-nitrobenzyl (1R,5S,6S)-2-[(3S,5S)-5-N,N-dimethylaminocarbonyl-1-isobutyryloxymethyloxycarbonyl)pyrrolidin-3-ylthio]-6-[(1R)-1-hydroxyethyl]-1-methylcarbapen-2em-3-carboxylate In the same manner as in Example 8 using (2S,4S)-2-N, N-dimethylaminocarbonyl-4-mercapto-1-isobutyryloxymethyloxycarbonylpyrrolidine, the title compound was obtained.

$^1$H-NMR(CDCl$_3$, δ ppm): 1.17(6H,d), 1.27(3H,d), 1.33 (3H,d), 1.7–2.1, 2.5–2.9(4H,m), 2.8–4.4(13H,m), 4.6–5.8 (5H,m), 7.64, 8.20(4H,A$_2$'B$_2$'.

Example 11

Sodium (1R,5S,6S)-2-[(3S,5S)-5-N,N-dimethylaminocarbonyl-1-isobutyryloxymethyloxycarbonyl)pyrrolidin-3-ylthio]-6-[(1R)-1-hydroxyethy]- 1-methylcarbapen-2-em-3-carboxylate In the same manner as in Example 9 using p-nitrobenzyl (1R,5S,6S)-2-[(3S,5S)-5-N,N-dimethylaminocarbonyl-1-isobutyryloxymethyloxycarbonyl)pyrrolidin-3-ylthio]-6-[(1R)-1-hydroxyethyl]-1-methylcarbapen-2em-3-carboxylate, the title compound was obtained.

$^1$H-NMR(DMSO-d$_6$, δ ppm): 1.0–1.4(12H, 1.4–1.9, 2.5–2.7(3H,m), 2.83(3H,s), 3.02(3H,brs), 4.6–4.8(1H,t), 5.5–5.7(2H,m).

Example 12 pivaloyloxymethyl (1R,5S,6S)-2-[(3S,5S)-5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate Sodium (1R,5S,6S)-2-[(3S,5S)-5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate (913 mg) was dissolved in N,N-dimethylformamide (6 ml) and cooled to 5° C. Pivaloyloxymethyl iodide (700 mg) was added and the mixture was stirred at the same temperature for 1 hr and at 30° C. for 1 hr. Ethyl acetate (150 ml) was added and the mixture was washed with 5% brine (100 ml) and dried over anhydrous sodium sulfate.

Ethyl acetate was evaporated under reduced pressure and the residue was purified by silica gel column chromatography to give the title compound (336 mg).

IR(Nujol, cm$^{-1}$) 3445,1755,1724,1651.

$^1$H-NMR(CDCl$_3$, δ ppm): 1.14(3H,t), 1.22(9H,s), 1.26 (3H,d), 1.32(3H,d), 1.7–2.1, 2.4–2.8(3H,m), 2.38(2H,q), 2.96(3H,d), 3.09(3H,d), 3.0–4.4(7H,m), 4.73(1H,m), 5.6–5.8(2H,m), 5.88(2H,ABq).

Example 13 pivaloyloxymethyl (1R,5S,6S)-2-[(3S,5S)-(5-N,N-dimethylaminocarbonyl-1-propionyloxymethyloxycarbonyl)pyrrolidin-3-ylthio]-6-[(1R)-1-[hydroxyethyl]-1-methylcarbapen-2-em-3-carboxylate (1) Sodium (1R,5S,6S)-2-[(3S,5S)-5-N,N-dimethylaminocarbonylpyrrolidin-4-ylthio]6-[(1R)-1-hydroxyethyl]-1-methylcarbapen-2-em-3-carboxylate (31.3 g) was suspended in N,N-dimethylformamide (148 ml) and the suspension was cooled to 5° C. Pivaloyloxymethyl iodide (37.2 g) was added and after stirring at the same temperature for 1 hr, potassium carbonate (3.19 g) and pivaloyloxymethyl iodide (11.2 g) were added. After mixing for one hour at the same temperature, ethyl acetate (1050 ml) was added. The mixture was washed with saturated aqueous sodium hydrogencarbonate solution (175 ml) and 5% brine (500 ml), and dried over anhydrous sodium sulfate.

Ethyl acetate was evaporated under reduced pressure and the residue was purified by silica gel column chromatography to give pivaloyloxymethyl (1R,5S,6S)-2-[(3S,5S)-5-N,N-dimethylaminocarbonylpyrrolidin-4-ylthio]-6-[(1R)-1-hydroxyethyl]-1-methylcarbapen-2-em-3-carboxylate (14.2 g).

$^1$H-NMR(CDCl$_3$, δ ppm): 1.22(9H,s), 1.2–1.4(6H,m), 1.5–1.8, 2.4–2.8(2H,m), 2.98(3H,s), 3.02(3H,s), 3.0–4.4 (8H,m), 5.81, 5.95(2H,ABq).

(2) The compound (9.5 g) obtained in (1) was dissolved in dichloromethane (50 ml) and propionyloxymethyl p-nitrophenyl carbonate (3.42 g) was added at 5° C. After stirring the mixture at the same temperature for 5 min and at room temperature for 1.5 hr. The reaction mixture was purified by silica gel column chromatography to give the title compound (1.1 g).

Example 14 pivaloyloxymethyl (1R,5S,6S)-2-[(3S,5S)-(5-N,N-dimethylaminocarbonyl-1-acetyloxymethyloxycarbonyl)pyrrolidin-3-ylthio]-6-[(1R)-1-hydroxyethyl]-1-methylcarbapen-2-em-3-carboxylate The compound (600 mg) obtained in Example 13 (1) was dissolved in N,N-dimethylformamide (3.5 ml). Acetyloxymethyl p-nitrophenyl carbonate (200 mg) and triethylamine (0.16 ml) were added, and the mixture was stirred at room temperature for 2 hr. Ethyl acetate (100 ml) was added, and the mixture was washed with 10% citric acid (100 ml), 5% aqueous sodium hydrogencarbonate solution (100 ml) and saturated brine (100 ml) and dried over anhydrous sodium sulfate. Ethyl acetate was evaporated under reduced pressure and the residue was purified by silica gel column chromatography to give the title compound (310 mg).

IR(Nujol, cm$^{-1}$): 3422,1760,1724,1647.

$^1$H-NMR(CDCl$_3$, δ ppm): 1.22(9H,s), 1.27(3H,d), 1.33 (3H,d), 1.7–2.1, 2.5–2.9(3H,m), 2.11(3H,s), 2.97(3H,d), 3.08(3H,d), 3.1–4.4(7H,m), 4.73(1H,m), 5.6–5.8(2H,m), 5.89(2H,ABq).

Example 15 pivaloyloxymethyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2-em-3-carboxylate The compound (550 mg) obtained in Example 13 (1) was dissolved in dichloromethane (3.5 ml). Isobutyryloxymethyl p-nitrophenyl carbonate (210 mg) was added, and the mixture was washed at room temperature for 2 hr. Ethyl acetate (100 ml) was added, and the mixture was washed with 10% citric acid (100 ml), 5% aqueous sodium hydrogencarbonate solution (100 ml) and saturated brine (100 ml) and dried over anhydrous sodium sulfate. Ethyl acetate was evaporated under reduced pressure and the residue was purified by silica gel column chromatography to give the title compound (210 mg).

IR(Nujol, cm$^{-1}$): 3385,1796,1753,1730,1636.

$^1$H-NMR(CDCl$_3$, δ ppm): 1.15(6H,d), 1.22(9H,s), 1.26 (3H,d), 1.33(3H,d), 1.7–2.1, 2.5–2.9(4H,m), 2.95(3H,d), 3.09(3H,d), 3.1–4.4(7H,m), 4.73(1H,n), 5.6–5.8(2H,m), 5.88(2H,ABq).

Example 16 pivaloyloxymethyl (1R,5S,6S)-2-[(3S,5S)-5-N,N-dimethylaminocarbonyl-1-pivaloyloxymethyloxycarbonyl)pyrrolidin-3-ylthio]-6-[(1R)-1-hydroxyethyl]-1-methylcarbapen-2-em-3-carboxylate The compound (580 mg) obtained in Example 13 (1) was dissolved in dichloromethane (3.5 ml). Pivaloyloxymethyl p-nitrophenyl carbonate (200 mg) was added, and the mixture was stirred at room temperature for 2 hr. Ethyl acetate (100 ml) was added, and the mixture was washed with 5% aqueous sodium hydrogencarbonate solution (100 ml) and saturated brine (100 ml) and dried over anhydrous sodium sulfite. Ethyl acetate was evaporated under reduced pressure and the residue was purified by silica gel column chromatography to give the title compound (300 mg).

IR(Nujol, cm$^{-1}$): 3423,1777,1751,1726,1649.

$^1$H-NMR(CDCl$_3$, δ ppm): 1.22(18H,s), 1.26(3H,d), 1.33 (3H,d), 1.7–2.1, 2.5–2.9(3H,m), 2.96(3H,s), 3.09(3H,d), 3.1–4.4(7H,m), 4.73(1H,m), 5.6–5.8(2H,m), 5.88(2H,ABq).

Example 17 pivaloyloxymethyl (1R,5S,6S)-2-[(3S,5S)-(5-N,N-dimethylaminocarbonyl-1-isovaleryloxymethyloxycarbonyl)pyrrolidin-3-ylthio]-6-[1(1R)-1-hydroxyethyl]-1-methylcarbapen-2-em-3-carboxylate In the same manner as in Example 16, the title compound was obtained.

$^1$H-NMR(CDCl$_3$, δ ppm): 0.96(6H,d), 1.22(9H,s), 1.26 (3H,d), 1.33(3H,d), 1.5–2.9(6H,m), 2.97(3H,s), 3.09(3H,d), 3.1–4.4(7H,m), 4.73(1H,m), 5.6–5.8(2H,m), 5.87(2H,ABq).

Example 18 pivaloyloxymethyl (1R,5S,6S)-2-[(3S,5S)-(5-N,N-dimethylaminocarbonyl-1-t-butylacetyloxymethyloxycarbonyl)pyrrolidin-3-ylthio]-6-[(1R)-1-hydroxyethyl]-1-methylcarbapen-2-em-3-carboxylate In the same manner as in Example 16, the title compound was obtained.

$^1$H-NMR(CDCl$_3$, δ ppm): 0.98(9H,s), 1.22(9H,s), 1.26 (3H,d), 1.33(3H,d), 1.7–2.9(5H,m), 2.96(3H,s), 3.08(3H,d), 3.1–4.4(7H,m), 4.73(1H,m), 5.6–5.8(2H,m), 5.87(2H,ABq).

Example 19

1-cyclohexyloxycarbonyloxyethyl (1R,5S,6S)-2-[(3S,5S)-(5-N,N-dimethylaminocarbonyl-1-isobutyryloxymethyloxycarbonyl)pyrrolidin-3-ylthio]-6-(1R)-1-hydroxyethyl]-1-methylcarbapen-2-em-3-carboxylate 1-Cyclohexyloxycarbonyloxyethyl (1R,5S,6S)-2-[(3S,5S)-(5-N,N-dimethylaminocarbonyl)pyrrolidin-3-ylthio]-6-[(1R)-1-hydroxyethyl]-1-methylcarbapen-2-em-3-carboxylate (1.00 g) obtained in the same manner as in Example 13 (1) was dissolved in dichloromethane (10 ml). Isobutyryloxymethyl p-nitrophenyl carbonate (500 mg) was added and the mixture was stirred at room temperature for 2 hr. The solvent was evaporated and the residue was purified by silica gel column chromatography to give the title compound (355 mg).

$^1$H-NMR(CDCl$_3$, δ ppm):1.0–2.1(27H,m), 2.96(3H,s), 3.06, 3.09(3H,s), 3.0–4.4(7H,m), 4.73(1H,m), 5.6–5.8(2H, m), 6.7–7.0(1H,q).

Example 20

1-ethoxycarbonyloxyethyl (1R,5S,6S)-2-[(3S,5S) - (5-N,N-dimethylaminocarbonyl-1-pivaloyloxymethyloxycarbonyl)pyrrolidin-3-ylthio]-6-[(1R)-1-hydroxyethyl]-1-methylcarbapen-2-em-3-carboxylate In the same manner as in Example 19, the title compound was obtained.

$^1$H-NMR(CDCl$_3$, δ ppm): 1.22(3H,t), 1.22(9H,s), 1.27 (3H,d), 1.32(3H,d), 1.51(3H,d), 1.6–2.0, 2.5–2.8(2H,m), 2.8–4.4(15H,m), 4.73(1H,m), 5.6–5.8(2H,m), 6.7–7.0(1H, q).

Experimental Example

The following oral absorption tests were performed as in the following to clarify the superior property of the compound of the present invention.

Experimental Example 1 (Oral Absorption Test)

The compound of the present invention (100 mg/kg, compound of Example 13) was orally administered to mice (3 per group) and the concentration of hydrolyzed carbapenem compound (A) in plasma was determined at 0.25, 0.5, 1.0, 2.0 and 3.0 hours later by HPLC. The results are shown in Table 1.

TABLE 1

| Test compound | Average concentration in plasma (μg/ml) | | | | |
|---|---|---|---|---|---|
| | 0.25 hr | 0.5 hr | 1.0 hr | 2.0 hr | 3.0 hr |
| Example 13 | 9.5 | 4.8 | 1.9 | 0.6 | 0.2 |

Experimental Example 2 (Oral Absorption Test)

The compound of the present invention (100 mg/kg, compound of Example 15) was orally administered to mice (3 per group) and the concentration of hydrolyzed carbapenem compound (A) in plasma was determined at 0.25, 0.5, 1.0, 2.0 and 3.0 hours later by HPLC. The results are shown in Table 2.

TABLE 2

| Test compound | Average concentration in plasma (μg/ml) | | | | |
|---|---|---|---|---|---|
| | 0.25 hr | 0.5 hr | 1.0 hr | 2.0 hr | 3.0 hr |
| Example 15 | 8.6 | 10.1 | 4.8 | 1.4 | 0.3 |

INDUSTRY APPLICABILITY

The carbapenem compound (I) of the present invention is superior in absorption from the digestive tract by oral administration and shows sufficient antibacterial property against a broad range of bacteria species. Therefore, the compound is extremely useful for the prophylaxis and treatment of infectious diseases (particularly bacterial infectious diseases). The inventive agent for the prophylaxis and treatment of infectious diseases can be used against diseases caused by bacteria in warm-blooded animals inclusive of human (e.g., dog, cat, cow, horse, rat, mouse and the like), such as purulent diseases, infection of respiratory organ, biliary tract infection, urinary tract infection and the like. In addition, carbapenem compound (II) is useful as an intermediate compound for carbapenem compound (I).

This application is based on application Nos. 122499/1998 and 203730/1998 filed in Japan, the contents of which are incorporated hereinto by reference.

What is claimed is:

1. A carbapenem compound of the formula (I)

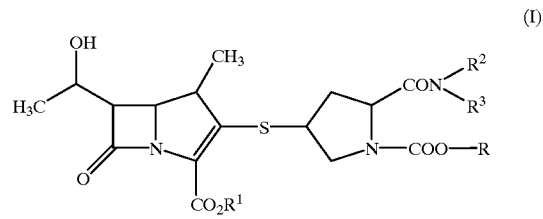

(I)

wherein R$^1$ is a group hydrolyzable in the living body, R$^2$ and R$^3$ are the same or different and each is a lower alkyl, R is a group of the formula (B)

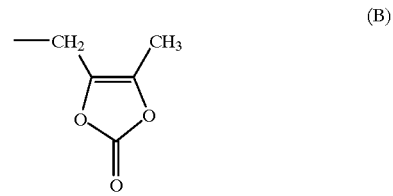

(B)

or formula (C)

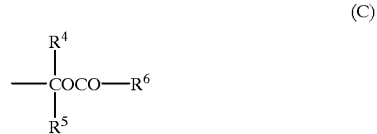

(C)

wherein R$^4$ and R$^5$ are the same or different and each is a hydrogen atom or a lower alkyl and R$^6$ is an alkyl having 1 to 10 carbon atoms.

2. The carbapenem compound of claim 1, wherein $R^2$ and $R^3$ are the same or different and each is a lower alkyl.

3. The carbapenem compound of claim 1, wherein $R^1$ is pivaloyloxymethyl.

4. The carbapenem compound of claim 1, wherein $R^1$ is 1-cyclohexyloxycarbonyloxyethyl.

5. The carbapenem compound of claim 1, wherein $R^1$ is 1-ethoxycarbonyloxyethyl.

6. The carbapenem compound of claim 1, which is a member selected from the group consisting of:
pivaloyloxymethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
1-cyclohexyloxycarbonyloxyethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
1-ethoxycarbonyloxyethyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
pivaloyloxymethyl (1R,5S,6S)-2-[(3S,5S)-(5-N,N-dimethylaminocarbonyl-1-acetyloxyethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[3S,5S)-(5-N,N-dimethylaminocarbonyl-1-isobutyryloxymethylcarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N,N-dimethylaminocarbonyl-1-pivaloyloxymethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N,N-dimethylaminocarbonyl-1-isovaleryloxymethyloxycarbonyl)pyrrolidin-3-ylthio]-6-[(1R)-1-hydroxyethyl]-1-methylcarbapen-2-em-3-carboxylate,
pivaloyloxymethyl (1R,5S,6S)-2-[(3S,5S)-(5-N,N-dimethylaminocarbonyl-1-tert-butylacetyloxymethyloxycarbonyl)pyrrolidin-3-ylthio]-6-[(1R)-1-hydroxyethyl]-1-methylcarbapen-2-em-3-carboxylate,
1-cyclohexyloxycarbonyloxyethyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2-em-3-carboxylate, and
1-ethoxycarbonyloxyethyl (1R,5S,6S)-2-[(3S,5S)-(5-N,N-dimethylaminocarbonyl-1-pivaloyloxymethyloxycarbonyl)pyrrolidin-3-ylthio]-6-[(1R)-1-hydroxyethyl]-1-methylcarbapen-2-em-3-carboxylate.

7. An antibacterial agent comprising the carbapenem compound of claim 1 having the formula (I) as an active ingredient, and a pharmaceutically acceptable excipient.

8. The antibacterial agent of claim 7, which is for oral administration.

9. A carbapenem compound of the formula (II)

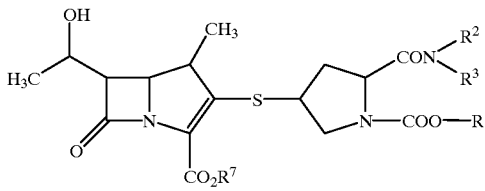

(II)

wherein $R^2$ and $R^3$ are the same or different and each is a lower alkyl, $R^7$ is a hydrogen atom or a protecting group of carbonyl group and R is a group of the formula (B)

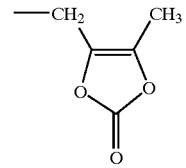

(B)

or formula (C)

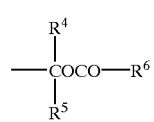

(C)

wherein $R^4$ and $R^5$ are the same or different and each is a hydrogen atom or a lower alkyl and $R^6$ is an alkyl having 1 to 10 carbon atoms,
or a salt thereof.

10. The carbapenem compound of claim 9, which is a member selected from the group consisting of:
p-nitrobenzyl (1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylate,
(1R,5S,6S)-2-{(3S,5S)-[5-N,N-dimethylaminocarbonyl-1-(5-methyl-2-oxo-1,3-dioxolen-4-yl)methyloxycarbonyl]pyrrolidin-3-ylthio}-6-[(1R)-1-hydroxyethyl]-1-methylcarbapen-2-em-3-carboxylic acid,
p-nitrobenzyl (1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylate,
p-nitrobenzyl (1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2-em-3-carboxylate,
(1R,5S,6S)-2-[(3S,5S)-(5-N,N-dimethylaminocarbonyl-1-propionyloxymethyloxycarbonyl)pyrrolidin-3-ylthio]-6-[(1R)-1-hydroxyethyl]-1-methylcarbapen-2-em-3-carboxylic acid, and
(1R,5S,6S)-2-[(3S,5S)-(5-N,N-dimethylaminocarbonyl-1-isobutyryloxymethyloxycarbonyl)pyrrolidin-3-ylthio]-6-[(1R)-1-hydroxyethyl]-1-methylcarbapen-2-em-3-carboxylic acid,
or a salt thereof.

11. The carbapenem compound of claim 10 or a salt thereof, wherein the salt is a sodium salt.

* * * * *